United States Patent [19]
Gabbard et al.

[11] Patent Number: 6,019,751
[45] Date of Patent: Feb. 1, 2000

[54] UNIVERSAL CONNECTOR AND A MEDICAL CONTAINER

[75] Inventors: Mark E. Gabbard, Salisbury, Md.; John J. Niedospial, Jr., Burlington, N.J.; Timothy J. Gabbard, Salisbury, Md.

[73] Assignee: Bracco Research USA, Princeton, N.J.

[21] Appl. No.: 09/009,487

[22] Filed: Jan. 20, 1998

[51] Int. Cl.[7] .................................. A61B 19/00
[52] U.S. Cl. .................. 604/408; 604/415; 215/247; 206/828
[58] Field of Search .................. 604/403, 408, 604/411–414, 415; 215/247, 249; 206/828

[56] References Cited

U.S. PATENT DOCUMENTS

| | | |
|---|---|---|
| 5,071,413 | 12/1991 | Utterberg . |
| 5,360,413 | 11/1994 | Leasont et al. . |
| 5,391,150 | 2/1995 | Richmond . |
| 5,573,516 | 11/1996 | Tyner . |

*Primary Examiner*—John G. Weiss
*Assistant Examiner*—Dennis Ruhl
*Attorney, Agent, or Firm*—Imre Balogh

[57] ABSTRACT

Universal connector designed for use in various containers having a fluid port for access to the content of the container or for transferring fluid into the container. The universal connector incorporates an elastomeric membrane capable of being ruptured by an access means such as a luer connector or a syringe having a sharp or blunt cannula for fluid communication between the content of the container and the access means.

16 Claims, 12 Drawing Sheets

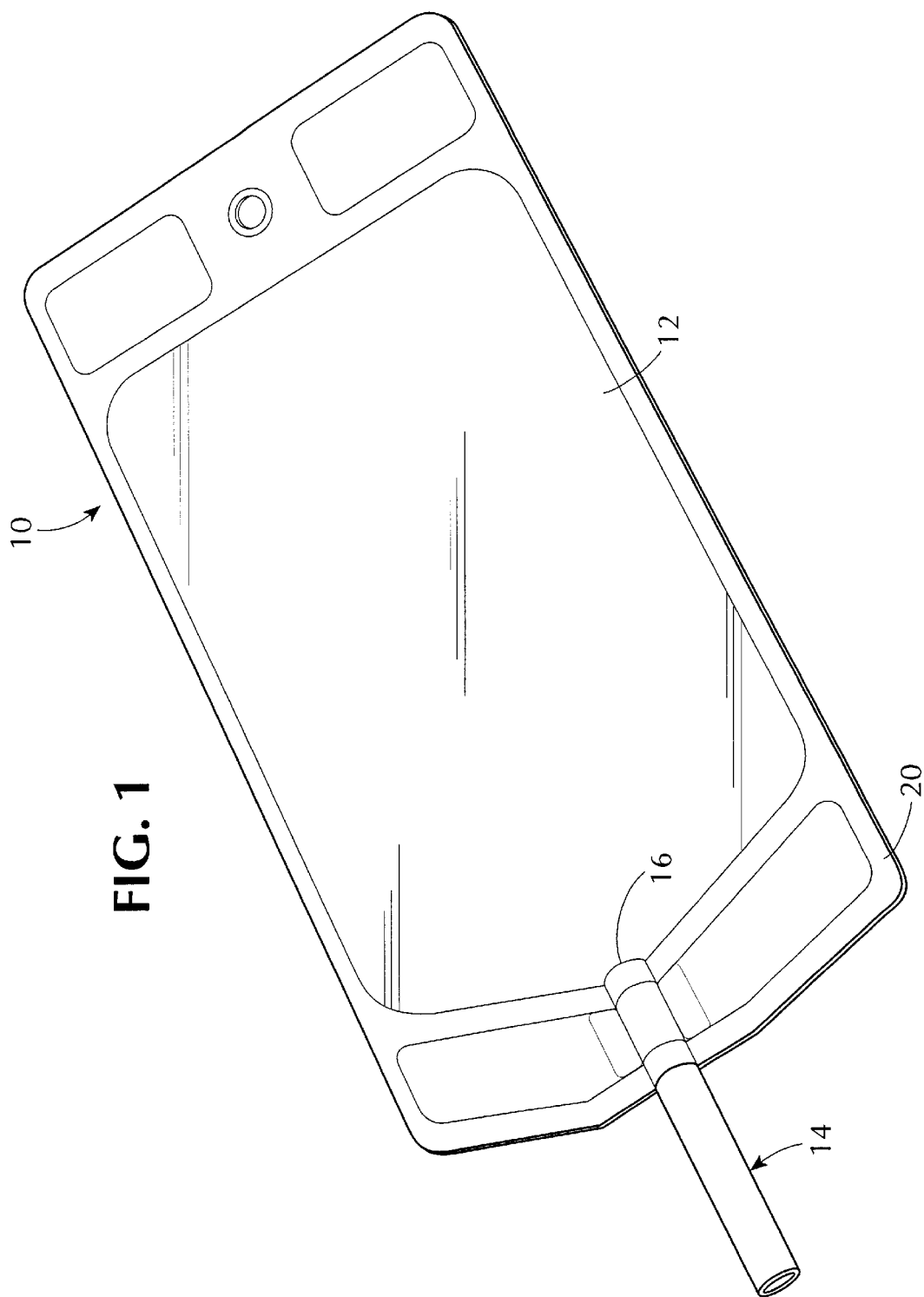

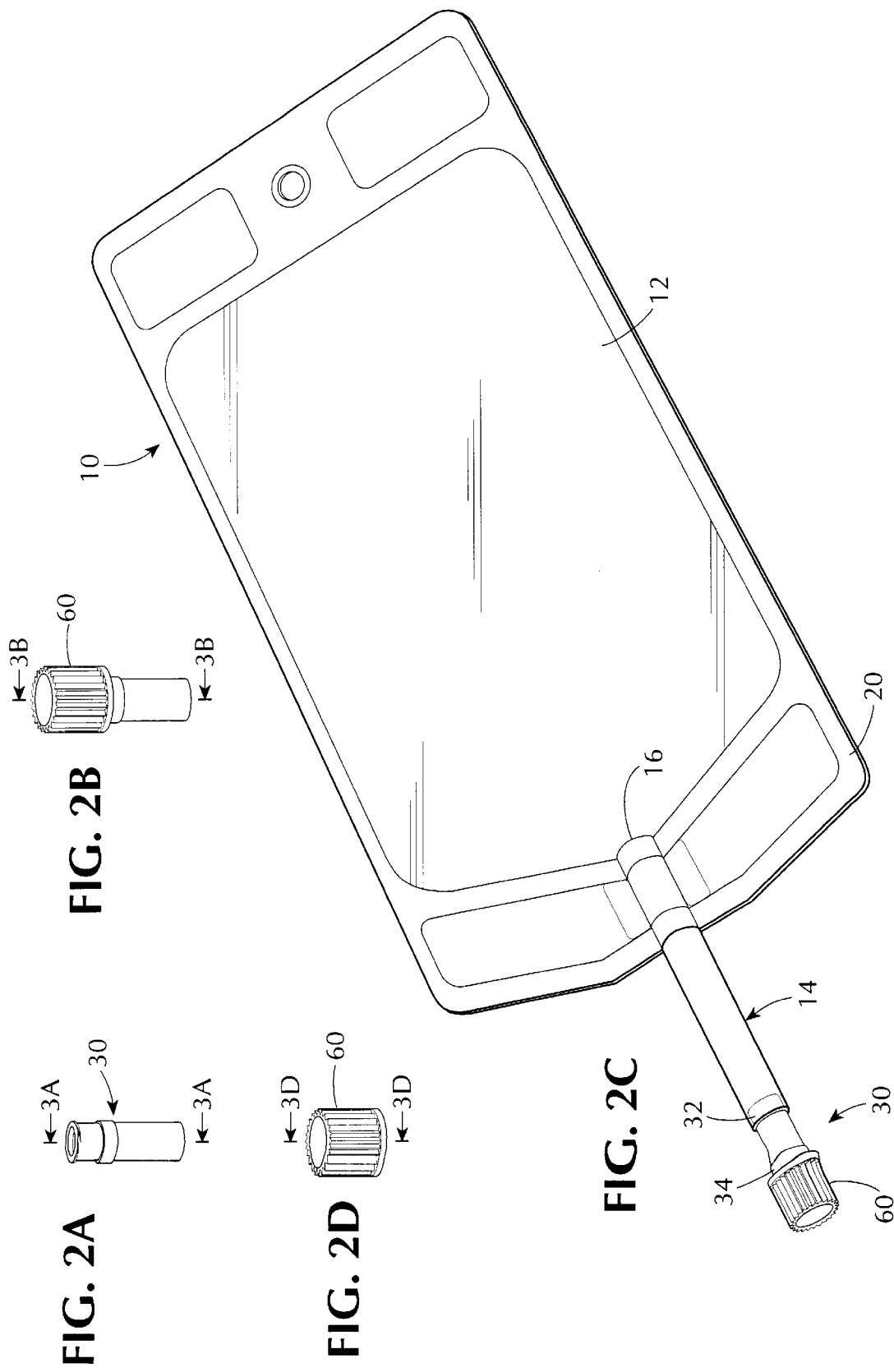

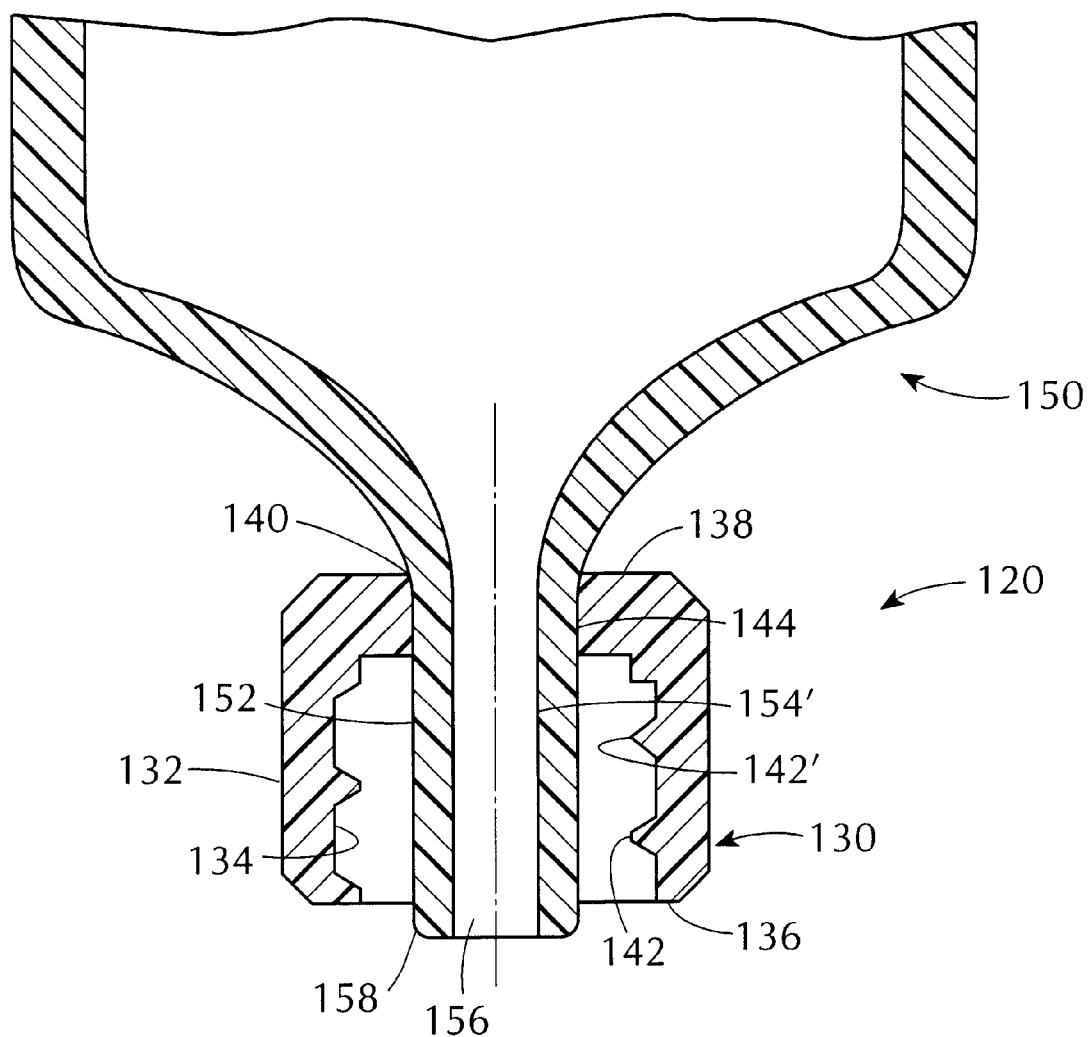

UNIVERSAL CONNECTOR AND A MEDICAL CONTAINER

BACKGROUND OF THE INVENTION

FIELD OF THE INVENTION

This invention relates to a universal connector connectable to containers having fluid contents therein designed for delivery to a site of administration. More particularly, the invention relates to a universal connector connectable to exit ports of collapsible bags and bottles such as intravenous (IV) bags.

REPORTED DEVELOPMENTS

Parenteral fluids, such as therapeutic drugs, diagnostic contrast media and nutrients are conventionally administered to a patient from a container, such as a collapsible bag or bottle having a fluid exit port. The fluid exit port may include means, such as a tube, spike or cannula, the distal end of which is in communication with the fluid content of the container and the proximal end of which is connected to the desired site on the patient. Conventionally, the proximal end of said means includes a needle that can puncture the patient. The fluid exit port is sealed by a membrane which is punctured by inserting a spike into the exit port when fluid delivery is desired. The membrane can also be a resealable membrane which after puncture reseals itself, due to its highly elastomeric properties, to prevent further fluid flow through the fluid exit port.

One approach used by the prior art to penetrate the membrane covering the fluid exit port comprises the use of syringes or spikes which carry the danger of accidental injuries caused by the sharp points of the needles and spikes. Such injuries accidentally inflicted on the health practitioner carry the further risk of getting infected with diseases such as AIDS. In order to reduce the danger of accidental injuries, spikes having relatively blunt tips were used. However, such pikes puncture a large area of the membrane and once the spikes are removed the membrane no longer seals the fluid exit port.

Another approach used by the prior art is the provision of a tubular member which is more blunt than a spike so that it is unlikely to penetrate the skin yet capable of penetrating the latex diaphragm type seals.

Still another approach used by the prior art is a valve positioned in the fluid exit port, the valve being operable by engagement with a spikeless or needleless IV component and contains a resilient valve disc positioned in the fluid passageway and blocks fluid flow when the disc is in the closed position, and allows fluid flow when the disc is in the open position.

Still another needleless connector of the prior art uses a resilient conical valve head in a housing. The conical valve head is positioned against the valve seat to form a seal. When the male fitting of a syringe, or some other device, is inserted into the inlet of the housing, it pushes the tip portion of the resilient valve head inwardly so that the valve head is deformed away from the valve seat thereby allowing fluid communication. In still other embodiments of the prior art, a needleless connector includes an elastomeric conical valve head biased against a conical valve seat by a helical spring to form a seal.

The above generally described devices have greatly reduced the use of syringes to withdraw medical fluids from collapsible bags and bottles thereby reducing needle-stick injuries and associated risks. The devices also advanced the prior art by providing convenient connectors which can be easily connected to the containers of medical fluids.

However, there still exists the need to provide a universal connector which may be used with a wide variety of connection sites. A seal or diaphragm is a main component of the herein-described invention which does not require penetration by any sharp or even blunt object in order to establish fluid communication between the content of the container and the site of delivery.

SUMMARY OF THE INVENTION

In accordance with the present invention there is provided a universal connector which can be used to access the fluid content of a container or to transfer a fluid into the container. The universal connector can be used in collapsible and non-collapsible bags, bottles and vials made of glass or polymeric material which contain a fluid exit port into which the universal connector is inserted sealing the fluid exit port. The fluid contained in the container may be a therapeutic liquid, diagnostic media or a nutritional formula which can be sterilized in bulk and then aseptically transferred into the container or it can be sterilized in the container stoppered with the universal connector. The universal connector is made of rigid or semi-rigid polymeric materials such as polyvinyl chloride, polyethylene and polypropylene.

The fluid in a container stoppered by the universal connector can be accessed by means well-known in the art, such as syringes having sharp or blunt needle cannulas. Preferably, the access means comprises a luer connector in order to prevent accidental injuries to health care workers and patients caused by the use of syringes.

The universal connector comprises:

(1) a connector body of tube-like configuration the distal end of which is designed to be slideably insertable into the fluid exit port, and the proximal end of which is designed to seal the content of the container by an elastomeric membrane and also to receive a removable cap; and (2) a removable cap threaded onto the proximal end of the connector which, prior to use, is removed so that the content of the container could be accessed by the use of a luer connector having a configuration that is similar to the configuration of the cap or by other access means, such as sharp or blunt needle cannulas.

The elastomeric membrane sealing the proximal end of the universal connector is of an inert, gas-impermeable polymeric material capable of flexing under internal or external pressures such as exerted thereon during steam sterilization. It preferably has a thickness of from about 0.001 mm to about 1.00 mm and a durometer of from about 25 to about 80 Shore A. It is capable of being ruptured by the twisting motion of a blunt luer connector or syringes having sharp or blunt needle cannula. The configuration of the elastomeric membrane is of cylindrical, however, preferred embodiments of the present invention include dome-shape, cone-shape, conic-section elastomeric membranes which can be ruptured or pierced even more readily by blunt access means than the cylindrical configuration embodiment.

The tube-like body of the universal connector further comprises: first cap-locking ring on the proximal end of the body which serves as a male thread to receive the removable cap; and second cap-locking ring spaced from the first cap-locking ring towards the distal end of the tube-like body, which serves as stopping means for the cap when the cap is threaded onto the tube-like body of the universal connector.

BRIEF DESCRIPTION OF THE DRAWINGS

FIG. 1 is a prospective view of a medical bag;

FIG. 2A is a perspective view of the universal connector of the present invention without the cap attached;

FIG. 2B is a perspective view of the universal connector of the present invention with the cap attached;

FIG. 2C is a perspective view of the universal connector of the present invention with the cap attached and connected to the medical bag of FIG. 1;

FIG. 2D is a perspective view of the cap;

FIG. 3AA is a top plan view of the universal connector without the cap attached of FIG. 3A;

FIG. 3CC is a top plan view of the cap shown in FIG. 2D;

FIG. 7 is a female luer connector attachable to the universal connector of the present invention.

DETAILED DESCRIPTION OF THE INVENTION

Figure 3A:
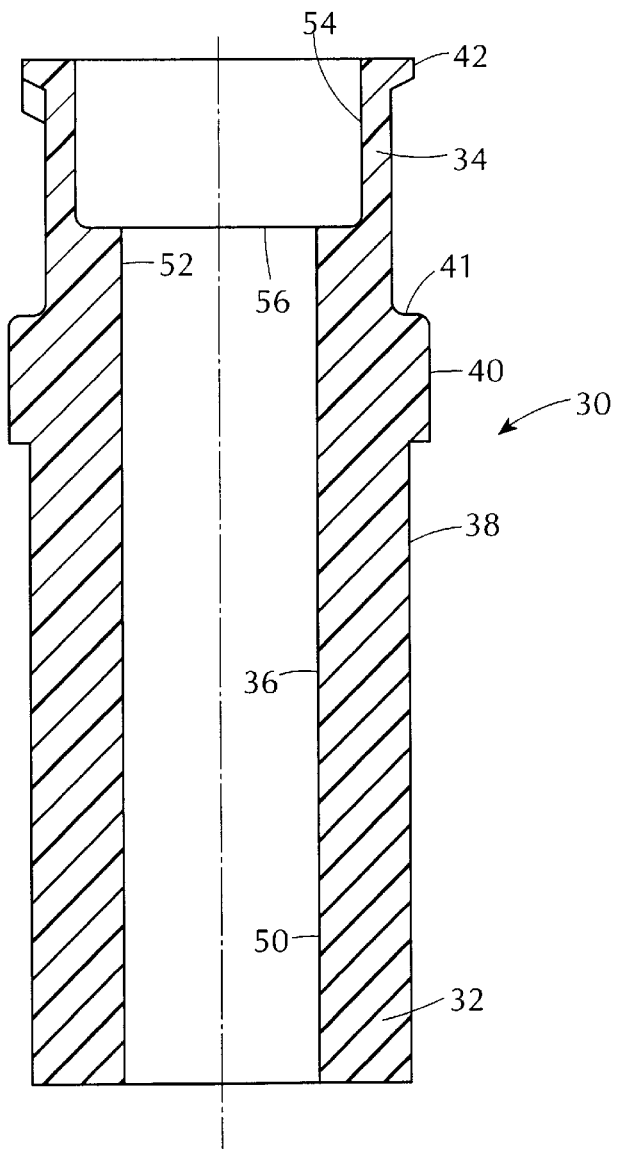
FIG. 3A is a cross-section of the universal connector without the cap attached taken along the line 3A—3A of FIG. 2A.
Figure 3A:
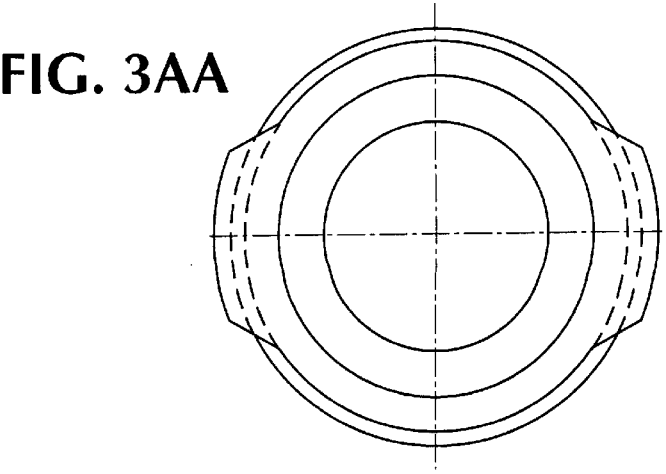

Referring to FIGS. 1, 2A, 2B, 2C and 2D, there is shown an intravenous bag 10 of conventional generally rectangular configuration made of inert, flexible, polymeric material, such as polyvinylchloride. The universal connector of the present invention will be described in reference to such flexible, polymeric bags, however, the universal connector can be used with other fluid containers such as bottles and vials of various configurations made of rigid or semi-rigid materials. Such containers will have fluid exit ports into which the universal connector can slideably be attached or it can be an integral part thereof The IV bag 10 contains a medical fluid 12 therein, such as a therapeutic, diagnostic or nutritional preparation. The medical fluid 12 may be pre-sterilized in bulk prior to its transfer to the IV bag, or it may be sterilized in the IV bag using sterilizing equipment and techniques known in the art. The IV bag further comprises a fluid exit port or tube 14 the distal end 16 of which is in communication with medical fluid 12 and the proximal end 18 of which is to slideably receive distal end 32 of universal connector 30. Alternatively, universal connector 30 may be integral with fluid exit port or tube 14 of IV bag 10. In both cases, fluid exit port or tube 14 is sealed into IV bag 10 by bottom seam 20 of IV bag 10. On the proximal end 34 of universal connector 30, cap 60 is mounted having internal thread means thereon for enclosing said proximal end 34. Prior to use, cap 60 is removed from universal connector 30 for engagement with a female luer connector.

FIG. 2A shows the universal connector without the cap; FIG. 2B shows the universal connector with the cap; and FIG. 2C shows the cap, all views being shows in perspective.

Figure 3B:
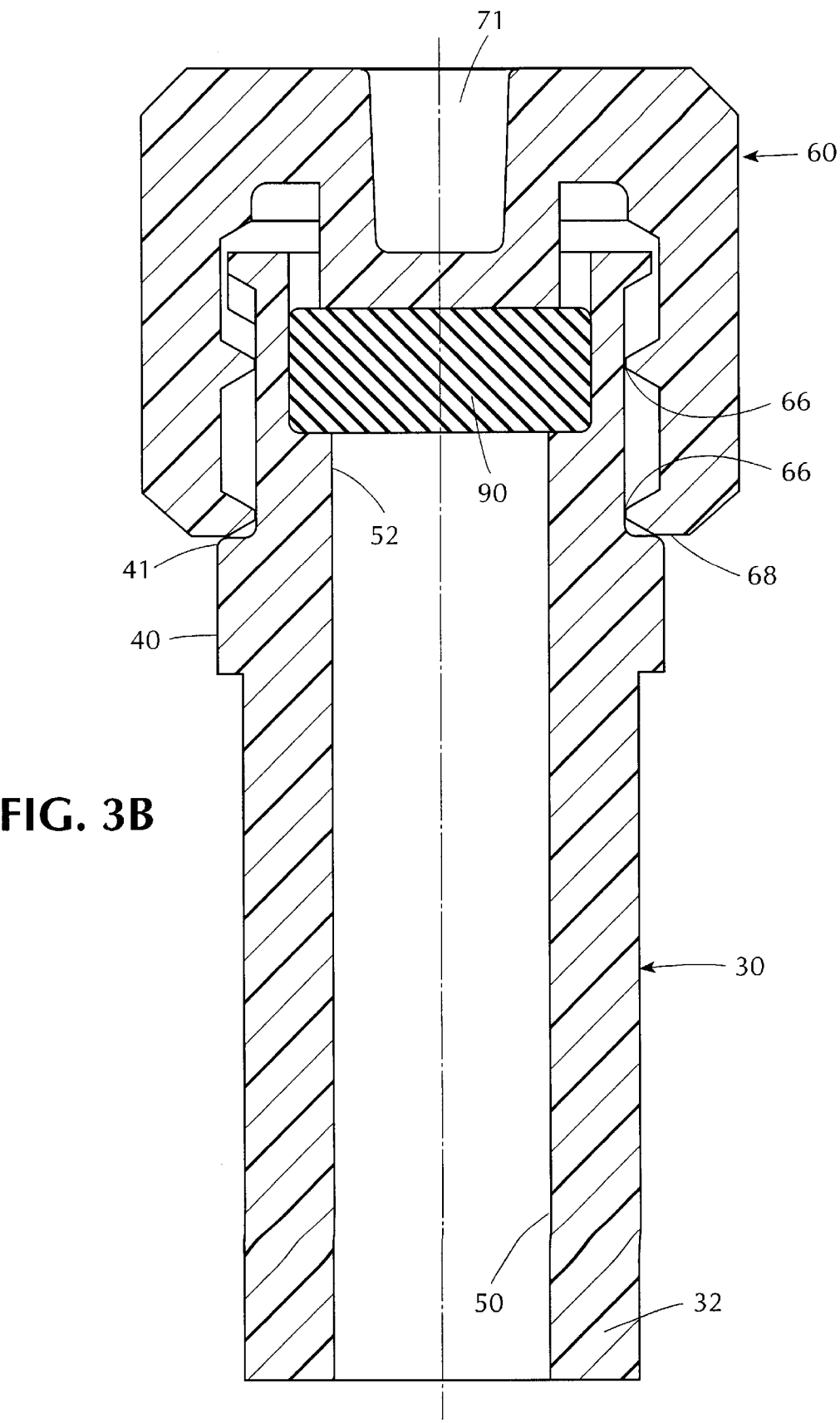
FIG. 3B is a cross-section of the universal connector with the cap attached taken along the line 3B—3B of FIG. 2B.
Figure 3C:
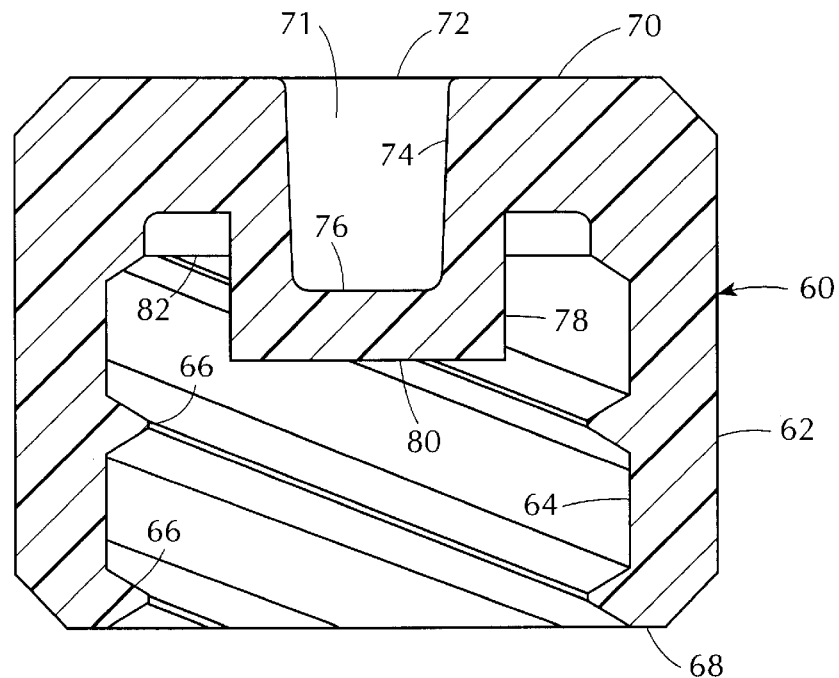
FIG. 3C is a cross-section of the cap taken along the line 3D—3D of FIG. 2D.
Figure 3C:
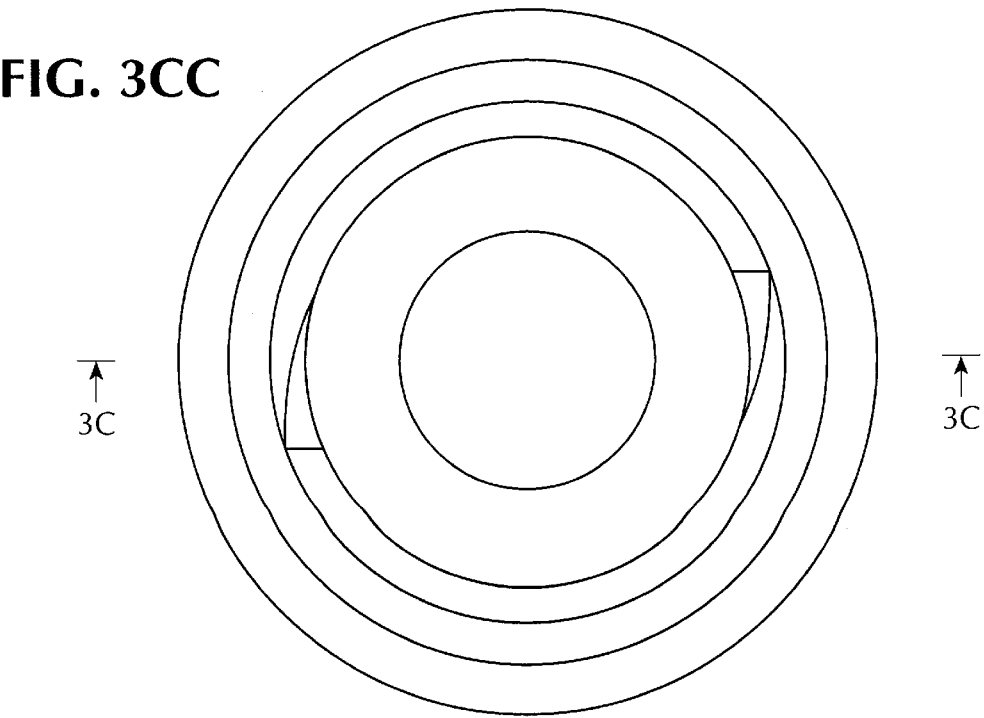

Reference is now being made to FIGS. 3A, 3AA, 3B, 3C and 3CC:

FIG. 3A shows a cross-sectional view of the universal connector without the cap taken along the line 3A—3A of FIG. 2A, and FIG. 3AA shows the top plan view thereof;

FIG. 3C shows a cross-section of the cap taken along the line 3D—3D of FIG. 2D, and FIG. 3CC shows the top plan view thereof; and FIG. 3B shows the universal connector assembly taken along the line 3B—3B of FIG. 2B.

Universal connector 30 is of tube-like configuration comprising: distal end 32 and proximal end 34; inside wall 36 and outside wall 38. Integral part of outside wall 38 at the proximal end 34 thereof is positioned first cap-locking ring 40 spaced from second cap-locking ring 42. First cap-locking ring serves as a male thread to receive cap 60 and to engage its internal threads 66 and 66'. Second cap-locking ring 40 having proximal end 41 has a larger external diameter than the distance defined by a line connecting internal threads 66–66' located at the proximal end 68 of cap 60. Second cap locking-ring 42 serves as stopping means for cap 60 when cap 60 is threaded onto universal connector 30.

Inside wall 36 of universal connector 30 comprises: a distal end 50 and proximal end 52. Distal end 50 is designed to slideably and sealingly engage fluid exit port or tube 14 to slide into the fluid exit port through its proximal end 18.

At the proximal end 52 of universal connector 30 a cylindrical opening is defined by side wall 54 and bottom wall 56. The cylindrical opening is designed to receive cylindrical protuberance defined by outside walls 78 and 80 of cap 60.

Bottom wall 56 of cylindrical opening in universal connector 30, as best can be seen in FIG. 3B, comprises a rubber or other elastomeric membrane 90 bonded to the universal connector. The elastomeric membrane is of cylindrical configuration and seals the fluid channel defined by the proximal end of inside wall 52 of universal connector 30. The membrane is of inert gas-impermeable polymeric material capable of flexing under internal or external pressures such as exerted during steam sterilization. Preferably the membrane has a thickness of from about 0.001 mm to about 1.00 mm and a durometer of from about 25 to about 80 Shore A. Suitable elastomeric materials for constructing the membrane include:

natural rubber;

acrylate-butadiene rubber;

cis-polybutadiene;

chlorobutyl rubber;

chlorinated polyethylene elastomers;

polyalkylene oxide polymers;

ethylene vinyl acetate;

fluorosilicone rubbers;

hexafluoropropylene-vinylidene fluoride-tetrafluoroethylene terpolymers, such as sold under the tradenames of Fluorel and Viton;

butyl rubbers;

polyisobutene, such as sold under the tradename Vistanex;

synthetic polyisoprene rubber;

silicone rubbers;

styrene-butadiene rubbers;

tetrafluoroethylene propylene copolymers; and thermoplastic-copolyesters.

As best can be seen in FIGS. 3C and 3CC, cap 60 is designed for securely closing universal connector 30 at the proximal end 34 thereof, and protecting elastomeric membrane 90 from contact with the outside environment. The configuration of the cap closely approximates the female luer connector shown in FIG. 7 which, in addition to the features detailed as the description of the cap proceeds, also contain a tubing conduit which is part of the female luer connector. FIGS. 3C and 3CC show cylindrical cap 60 comprising: outside wall 62 and inside wall 64. Outside wall 62 comprises: bottom wall 68; top wall 70; and central portion 72 of top wall 70. Inside wall 64 comprises: internal threads 66 and 66' extending towards the center of the cap; a cylindrical protuberance defined by outside wall 78 and bottom wall 80 extending distally into the space defined by the inside wall; and shoulder portion 82 connecting inside wall 64 and outside wall 78 of the cylindrical protuberance. In the proximal end of cap 60 there is located plug 71 defined by central portion 72 of top wall 70, and bottom wall 76. Plug 71 may be integral with the cap such as obtained by blow molding technique or, as shown in FIGS. 3C and 3CC, the plug may be manufactured separately and subsequently sealed into the cap.

Referring again to FIGS. 3A, 3B and 3C, when cap 60 is threaded onto universal connector 30, bottom wall of protuberance 80 will be spaced from elastomeric membrane 90 allowing the membrane to flex outward under pressure, such as created during heat sterilization. However, spacing should not be more than about 2 to 3 mm so that under accidentally high pressures, bursting of the membrane is prevented by the support of bottom wall 80 of cylindrical protuberance.

Figure 4:
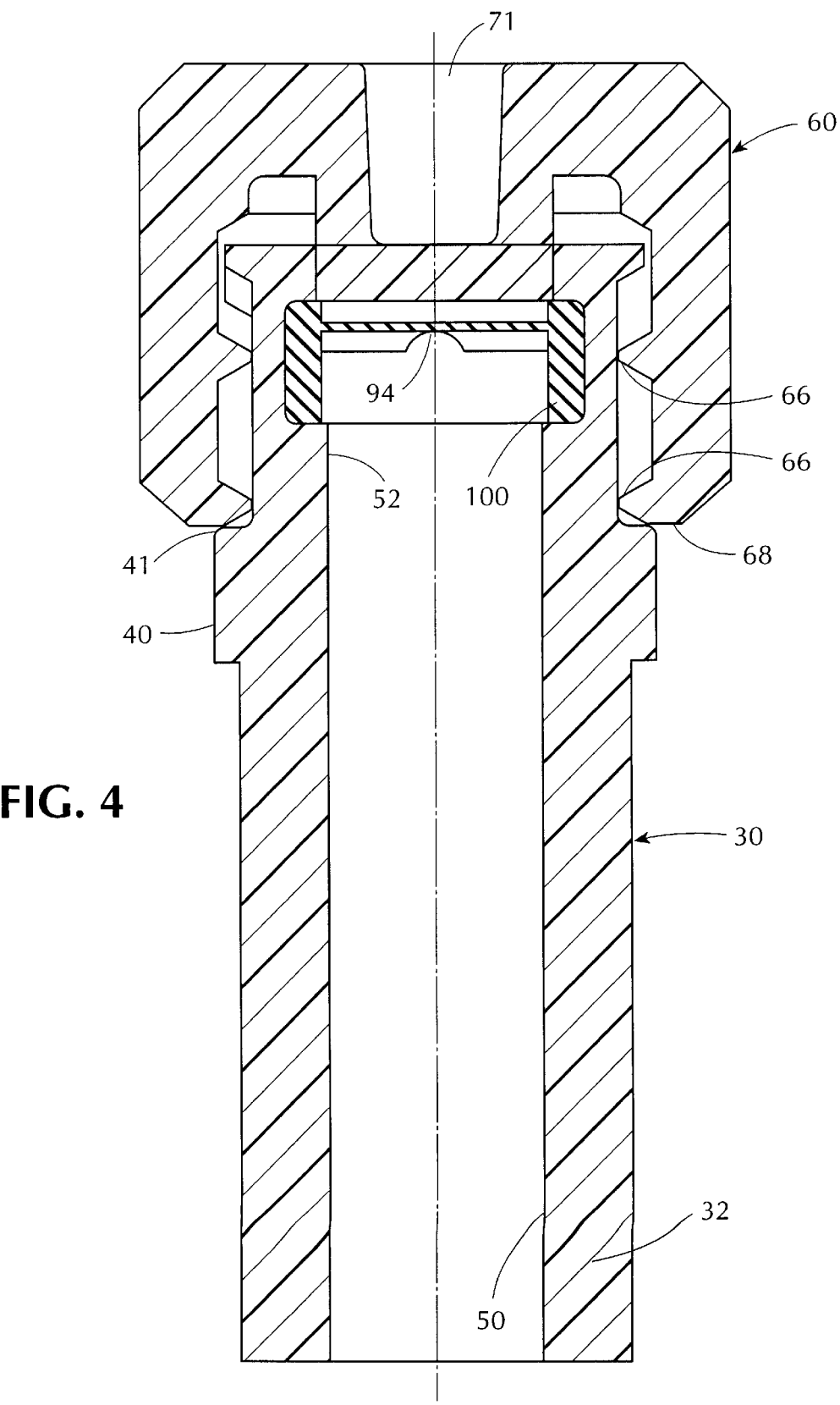
FIG. 4 is a cross-sectional view of another embodiment of the universal connector with the cap attached, showing a rubber seal having a generally dome-shaped configuration in the center thereof.
Figure 4A:
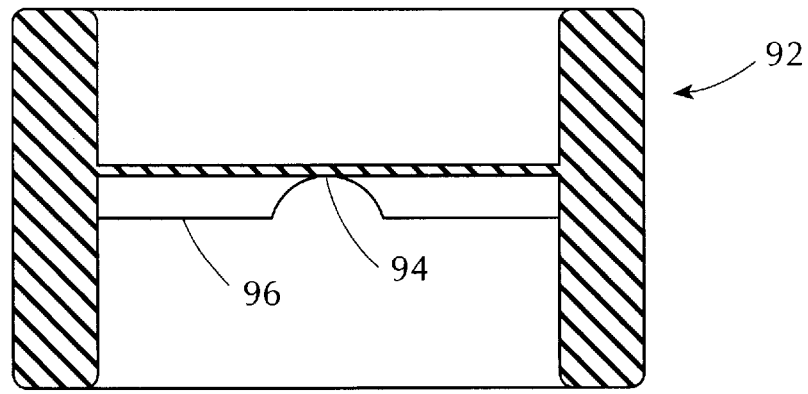
FIG. 4A is the rubber seal shown in cross-sectional view in FIG. 4 removed from the universal connector.
Figure 4B:
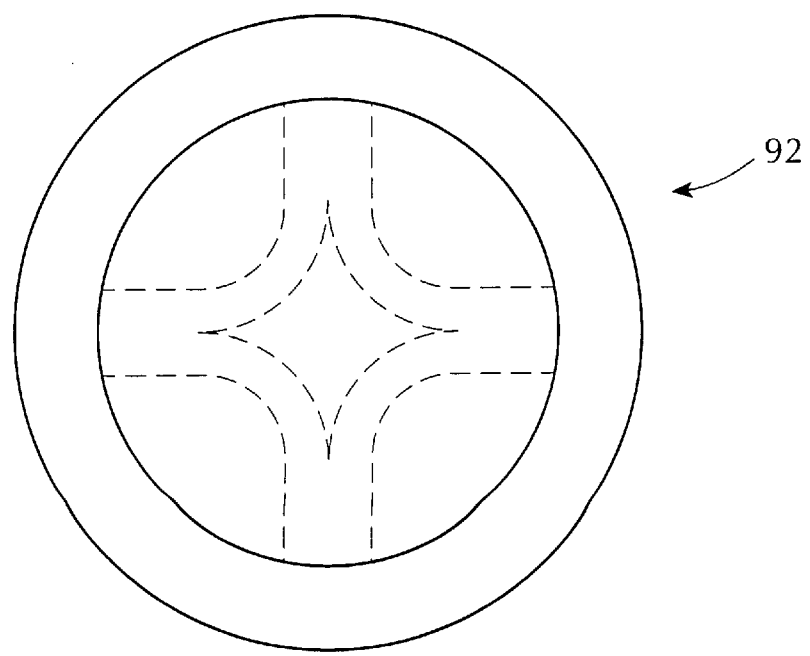
FIG. 4B is the top plan view of the rubber seal shown in cross-sectional view in FIG. 4A.

FIGS. 4, 4A and 4B show another embodiment of the universal connector of the present invention in cross-sectional view assembled with the cap wherein like numbers denote the same parts as in FIGS. 3A, 3AA, 3B, 3C and 3CC. The figures show a difference elastomeric membrane having a generally dome-shaped configuration in the center thereof Elastomeric membrane 92, shown in cross-section, is of cylindrical configuration and is bonded to universal connector 30. Preferably, the membrane has a thickness of from about 0.001 mm to about 1.00 mm and a durometer of from about 25 to about 80 Shore A. Suitable elastomeric materials constructing the membrane include those described for the embodiment described in the embodiment shown in FIG. 3A, 3AA, 3B, 3C and 3CC. The dome-shape configuration 94 rises above the horizontal portion 96 of elastomeric membrane 92 towards the distal end of universal connector 30 and has the same thickness as the horizontal portion 96 thereof The dome-shape configuration allows easy rupture of the membrane at 94 when female luer connector is threaded into universal connector 30 in order to establish fluid communication.

Figure 5:
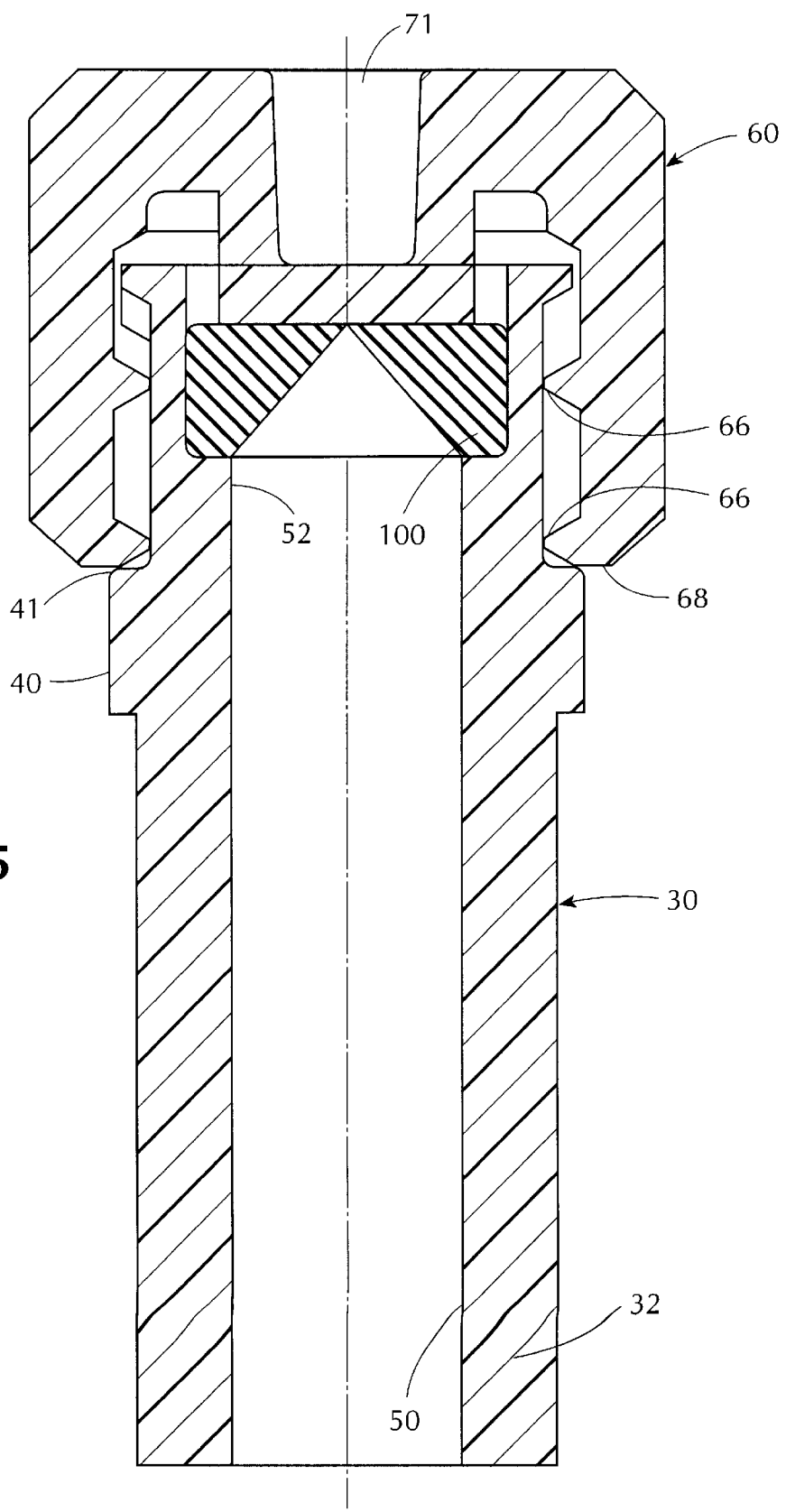
FIG. 5 is a cross-sectional view of still another embodiment of the universal connector with the cap attached, showing a rubber seal having a large generally cone-shaped configuration in the center thereof.
Figure 5A:
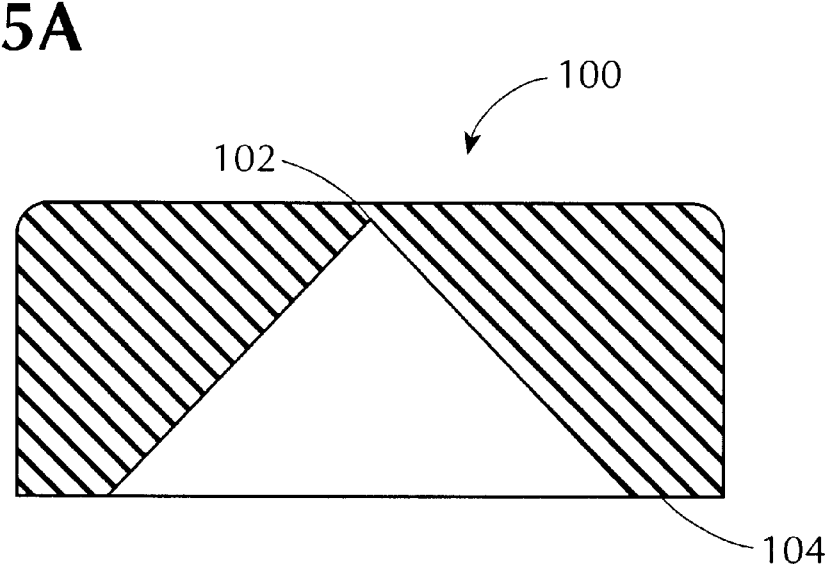
FIG. 5A is the rubber seal shown in cross-sectional view of FIG. 5 removed from the universal connector.
Figure 5B:
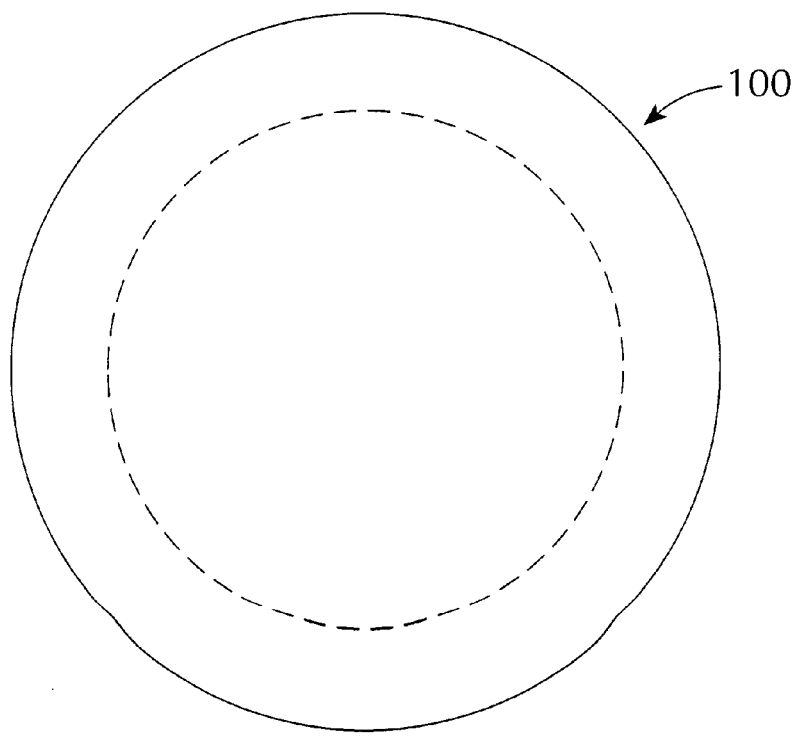
FIG. 5B is a top plan view of the rubber seal shown in cross-sectional view in FIG. 5A.

FIGS. 5, 5A and 5B show still another embodiment of the universal connector of the present invention in cross-sectional view assembled with the cap attached wherein like numbers denote the same parts as in FIGS. 3A, 3AA, 3B, 3C and 3CC. The figures show an elastomeric membrane 100 having a large generally cone-shaped 102 configuration in the center thereof The cone-shape configuration having a tip which rises above the horizontal portion 104 of elastomeric membrane 100 toward the distal end of the universal connector 30 and has from about 5% to about 20% of the thickness of the elastomeric membrane 100. The cone-shape configuration allows easy rupture of the membrane at 102 when female luer connector is threaded into universal connector 30 in order to establish fluid communication.

Figure 6:
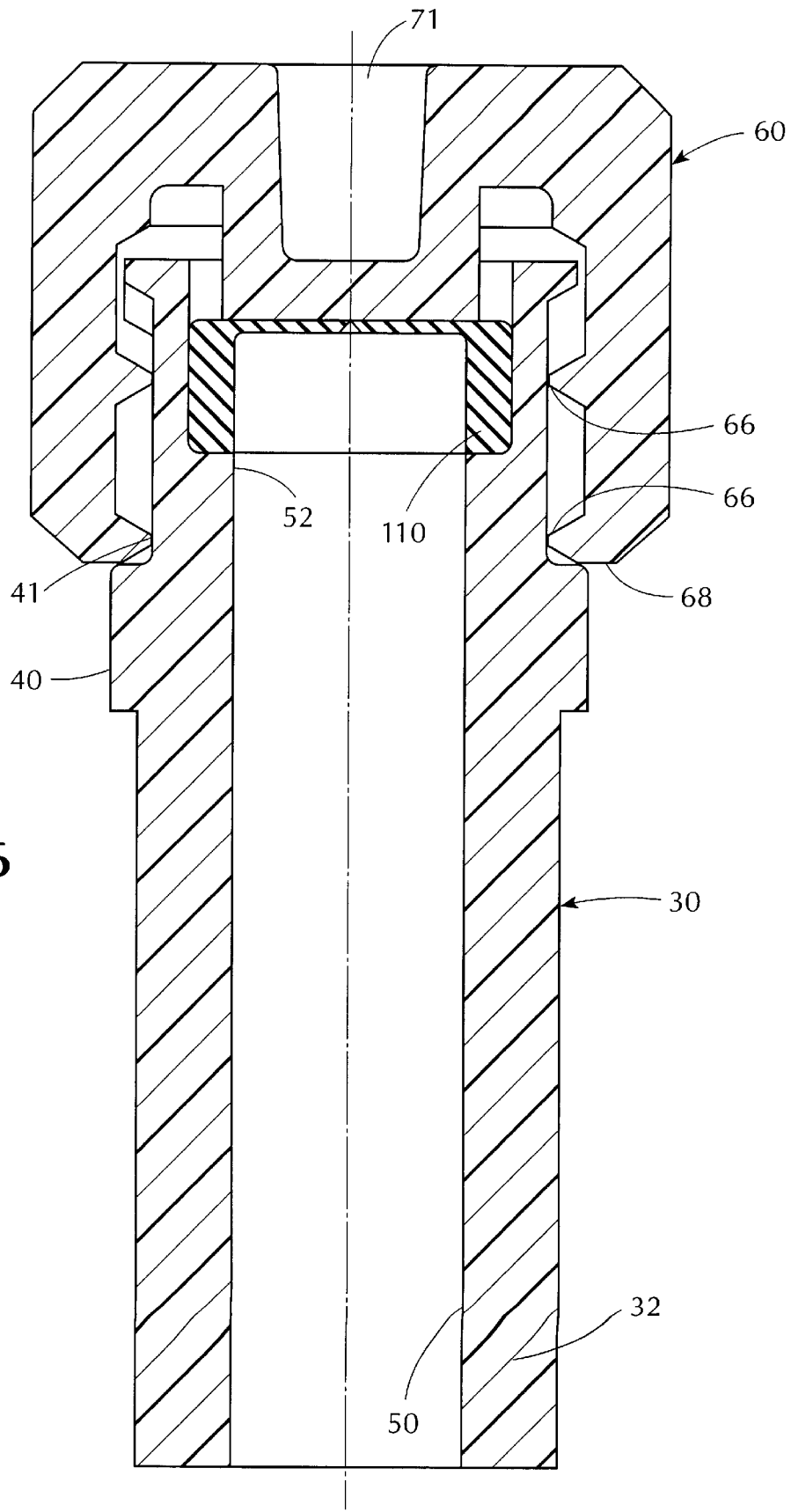
FIG. 6 is a cross-sectional view of still another embodiment of the universal connector with the cap attached, showing a rubber seal having a small, generally conic section configuration in the center thereof.
Figure 6A:
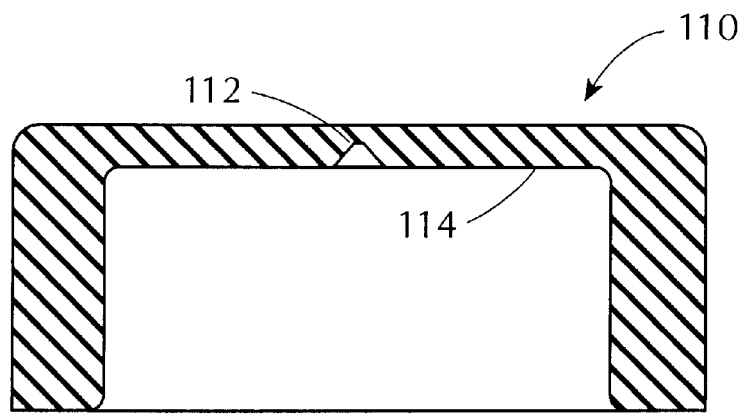
FIG. 6A is the rubber seal shown in cross-sectional view in FIG. 6 removed from the universal connector.
Figure 6B:
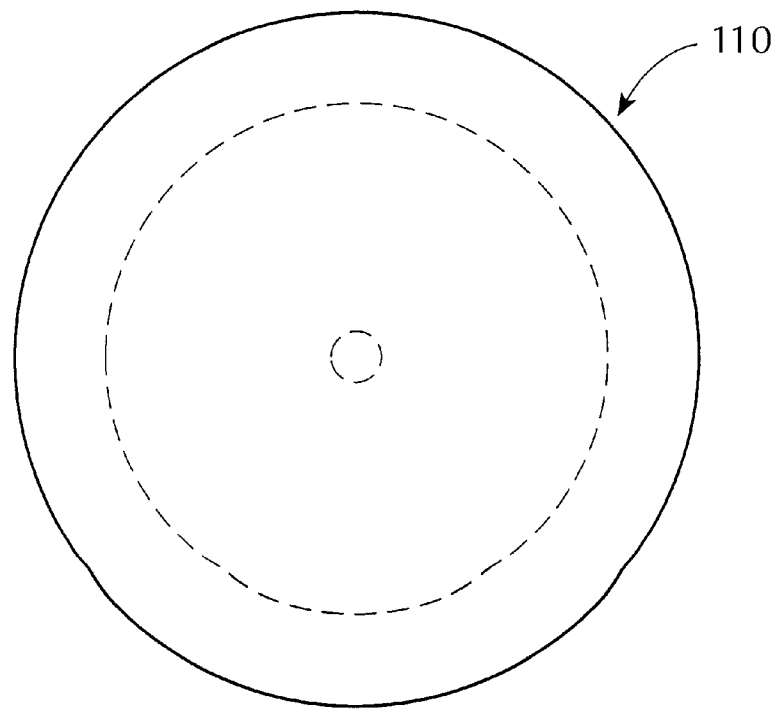
FIG. 6B is a top plan view of the rubber seal shown in cross-sectional view in FIG. 6A.

FIGS. 6, 6A and 6B show still another embodiment of the universal connector of the present invention in cross-sectional view assembled with the cap wherein like numbers denote the same parts as in FIGS. 3A, 3AA, 3B, 3C and 3CC. The figures show an elastomeric membrane 110 having a conic section configuration 112 in the center thereof which rises above the horizontal portion 114 of elastomeric membrane 110 towards the distal end of universal connector 30. The thickness of the elastomeric membrane above the conic section is of from about 10% to about 60% of the thickness of the horizontal portion 114 of elastomeric membrane 110. The conic section configuration allows easy rupture of the membrane at 112 when female luer connector is threaded into universal connector 30 in order to establish fluid communication.

FIG. 7 shows in cross-sectional view a female luer connector attachable to each of the embodiments of the present invention. The female luer connector 120 comprises a cylindrical cap 130 and tubing conduit 150. Cylindrical cap 130 closely approximates cylindrical cap 60 of universal connector shown in FIGS. 3C and 3CC and its function is to be threaded onto universal connector when fluid communication is desired. Prior to threading cylindrical cap 130 of female luer connector 120 onto universal connector 30, cylindrical cap 60 is removed and then replaced by cylindrical cap 130 of female luer-connector 120.

Cylindrical cap 130 of female luer connector 120 comprises outside wall 132 and inside wall 134. Outside wall 132 comprises: bottom wall portion 136; top wall portion 138; and central portion 140 of top wall portion 138. Inside wall 134 comprises: internal threads 142 and 142' extending towards the center of the cap.

Tubing conduit 150 is positioned in cylindrical cap 130 of female luer connector 120 at its top central portion 140. Thickened outside wall portion 144 parallelly faces outside wall 152 of tubing conduit 150 and is permanently attached thereto by adhesive or other suitable means known in the art. Tubing conduit further comprises: inside walls of tubing conduit 154 and 154' forming a fluid channel 156; and bottom end portion of tubing conduit 158 which extends beyond bottom portion 136 of cylindrical cap 60 of universal connector 30. When threaded onto universal connector 30, female luer connector 120 travels towards second cap-locking ring 42, contacts elastomeric membrane 90 or 92 or 100 or 110 with its bottom and portion 158 and exerts pressure thereon in a twisting motion. The exerted force ruptures the elastomeric membrane thereby allowing fluid communication between the female luer connector 120 and the content of the intravenous infusion bag.

The universal connector 30 may also be used in containers, such as bottles and vials the contents of which are intended to be accessed by a hypodermic syringe having either a sharp or blunt cannula. When fluid withdrawal or fluid addition is desired, cylindrical cap 60 of universal connector 30 is removed and the elastomeric membrane is pierced by the cannula providing access to the content of the container or withdrawal therefrom.

Intravenous infusion bag (IV bag) 10
Fluid contained in bag 12
Fluid exit port or tube in IV bag 14
Distal end of fluid exit port or tube 16
Proximal end of fluid exit port or tube 18
Bottom seam of IV bag 20
Universal connector 30
Distal end of universal connector 32
Proximal end of universal connector 34
Inside wall of universal connector 36
Outside wall of universal connector 38
First cap-locking ring 40
Proximal end of second locking-ring 41
Second cap-locking ring 42
Distal end of inside wall of universal connector 50
Proximal end of inside wall of universal connector 52
Side wall of cylindrical opening at proximal end of universal 54 connector
Bottom wall of cylindrical opening at proximal end of universal 56 connector
Cylindrical cap of universal connector 60
Internal threads on cap 66, 66'
Bottom wall of cap 68
Top wall of cap 70
Plug 71
Central portion of top wall 72
Side wall of plug 74
Bottom wall of plug 76
Outside wall of cylindrical protuberance of cap 78
Bottom wall of cylindrical protuberance of cap 80
Shoulder connecting inside wall of cap and outside wall of 82 cylindrical protuberance of cap
Elastomeric membrane 90, 92, 100, 110
Dome-shape configuration in center of elastomeric membrane 94
Horizontal portion of dome-shape membrane 96
Cone-shape configuration of elastomeric membrane 100 102
Horizontal portion of cone-shape membrane 102 104
Conic section in elastomeric membrane 110 112
Horizontal portion of elastomeric membrane 110 114
Female luer connector 120
Cylindrical cap of female luer connector 130
Top portion of cylindrical cap 138
Center top portion of cylindrical cap 140
Wall portion of cylindrical cap facing tubing conduit 150 144
Tubing conduit in female luer connector 150
Outside wall of tubing conduit 152
Inside wall of tubing conduit 154, 154'
Fluid channel 156
Bottom end portion of tubing conduit 158

Various modifications of the present invention disclosed will become apparent. This invention is intended to include such modifications to be limited only by the scope of the claims.

What is claimed is:

1. A universal connector-medical container assembly comprising:

a) a medical container having a medical fluid therein; and b) a universal connector wherein said medical container comprises a fluid access port for accessing the medical fluid contained therein or for transferring a medical fluid thereinto;

said universal connector comprising:

(1) a connector body of tube-like configuration having a distal end and a proximal end, wherein said distal end is designed to be slideably inserted into the fluid access port of said medical container and said proximal end is designed to seal the medical fluid content of said medical container by an elastomeric membrane and a removable cap;

said connector body comprising:

a first cap-locking ring on the proximal end of said connector body which serves as a male thread to receive said removable cap or a luer connector; and a second cap-locking ring, spaced from said first cap-locking ring towards the distal end of said connector body, which serves as stopping means for the removable cap or the luer connector when said removable cap or said luer connector are threaded onto the connector body;

(2) an elastomeric membrane of an inert, gas-impermeable polymeric material, capable of flexing under pressure, sealing said proximal end of said connector body; and (3) said removable cap threaded onto the proximal end of said connector body to protect said elastomeric membrane from environmental forces and maintain said elastomeric membrane in aseptic condition prior to removal of said removable cap to access said medical fluid content of said medical container or to transfer the medical fluid into said medical container by a fluid access or a transfer means.

2. The universal connector-medical container assembly of claim 1 wherein said elastomeric membrane has a thickness of from about 0.001 mm to about 1.0 mm and a durometer of from about 25 to about 80 Shore A.

3. The universal connector-medical container assembly of claim 1 wherein said elastomeric membrane is of an elastomeric material selected from the group consisting of:

natural rubber;

acrylate-butadiene rubber;

cis-polybutadiene;

chlorobutyl rubber;

chlorinated polyethylene elastomers;

polyalkylene oxide polymers;

ethylene vinyl acetate;

fluorosilicone rubbers;

hexafluoropropylene-vinylidene fluoride-tetrafluoroethylene terpolymers;

butyl rubbers;

polyisobutene;

synthetic polyisoprene rubber;

silicone rubbers;

styrene-butadiene rubbers;

tetrafluoroethylene propylene copolymers; and thermoplastic-copolyesters.

4. The universal connector-medical container assembly of claim 1 wherein said elastomeric membrane is cylindrical, dome-shape, cone-shape or conical configuration.

5. The universal connector-medical container assembly of claim 1 wherein said fluid access or transfer means comprises a luer connector or a syringe having a sharp or blunt needle cannula.

6. The universal connector-medical container assembly of claim 1 wherein said medical fluid is a therapeutic liquid.

7. The universal connector-medical container assembly of claim 1 wherein said medical fluid is a diagnostic media.

8. The universal connector-medical container assembly of claim 1 wherein said medical fluid is a nutritional liquid.

9. A method of withdrawing a medical fluid contained in a medical container or introducing a medical fluid into a medical container equipped with a universal connector comprising the steps of:

(A) providing a universal connector-medical container assembly comprising:
  a) the medical container having a medical fluid therein; and
  b) the universal connector wherein
    said medical container comprises a fluid port for allowing withdrawal of said medical fluid contained therein or for transferring a medical fluid thereinto;
    said universal connector comprising:
    (1) a connector body of tube-like configuration having a distal end and a proximal end, wherein said distal end is designed to be slideably inserted into the fluid port of said medical container and said proximal end is designed to seal the medical fluid content of said medical container by an elastomeric membrane and a removable cap;
      said connector body comprising:
        a first cap-locking ring on the proximal end of said connector body which serves as a male thread to receive said removable cap or a luer connector; and
        a second cap-locking ring, spaced from said first cap-locking ring towards the distal end of said connector body, which serves as stopping means for the removable cap or the luer connector when said removable cap or said luer connector are threaded onto the connector body;
    (2) an elastomeric membrane of an inert, gas-impermeable polymeric material, capable of flexing under pressure, sealing said proximal end of said connector body; and
    (3) a removable cap threaded onto the proximal end of said connector body to protect said elastomeric membrane from environmental forces and maintain said elastomeric membrane in aseptic condition prior to removal of said cap to withdrawal said medical fluid content of said medical container or to transfer said medical fluid into said medical container by a withdrawal or a transfer means;

(B) removing said removable cap from said connector body; and (C) withdrawing the medical fluid contained in said medical container or introducing a medical fluid into said medical container by a fluid access or a transfer means.

10. The method of claim 9 wherein said fluid access means is a female luer connector comprising:

(a) a cylindrical cap comprising: a distal rim portion, a proximal rim portion and an inside wall extending from the distal rim portion to the proximal rim portion, said inside wall having thread means thereon;

(b) a tubing conduit having a proximal end and a distal end and a fluid channel therein contained in said cylindrical cap and permanently attached to said cap by sealing means, wherein said proximal end of the tubing conduit extends beyond the proximal rim portion of said cylindrical cap and is designed to contact and rupture the elastomeric membrane when said cylindrical cap is threaded onto said universal connector to establish fluid communication with the medical fluid content of the medical container.

11. The method of claim 9 wherein said withdrawal or transfer means is a syringe having a sharp or blunt needle cannula.

12. The method of claim 9 wherein said elastomeric membrane has a thickness of from about 0.001 mm to about 1.0 mm and a durometer of from about 25 to about 80 Shore A.

13. The method of claim 9 wherein said elastomeric membrane is of an elastomeric material selected from the group consisting of:

natural rubber;

acrylate-butadiene rubber;

cis-polybutadiene;

chlorobutyl rubber;

chlorinated polyethylene elastomers;

polyalkylene oxide polymers;

ethylene vinyl acetate;

fluorosilicone rubbers;

hexafluoropropylene-vinylidene fluoride-tetrafluoroethylene terpolymers;

butyl rubbers;

polyisobutene;

synthetic polyisoprene rubber;

silicone rubbers;

styrene-butadiene rubbers;

tetrafluoroethylene propylene copolymers; and thermoplastic-copolyesters.

14. The method of claim 9 wherein said medical fluid is a therapeutic liquid.

15. The method of claim 9 wherein said medical fluid is a diagnostic liquid.

16. The method of claim 9 wherein said medical fluid is a nutritional liquid.

* * * * *